(12) United States Patent
Bergman

(10) Patent No.: US 7,011,099 B2
(45) Date of Patent: *Mar. 14, 2006

(54) FLOSSING DEVICE WITH ADVANCING AND TENSIONING MECHANISM

(76) Inventor: Mark C. Bergman, 13745 Seminole Dr., Chino, CA (US) 91710

( * ) Notice: Subject to any disclaimer, the term of this patent is extended or adjusted under 35 U.S.C. 154(b) by 0 days.

This patent is subject to a terminal disclaimer.

(21) Appl. No.: 10/635,425

(22) Filed: Aug. 5, 2003

(65) Prior Publication Data

US 2004/0134511 A1 Jul. 15, 2004

Related U.S. Application Data

(63) Continuation of application No. 09/861,254, filed on May 18, 2001, now Pat. No. 6,874,509.

(51) Int. Cl.
*A61C 15/00* (2006.01)

(52) U.S. Cl. .................................. 132/325; 132/324
(58) Field of Classification Search ......... 132/322–329
See application file for complete search history.

(56) References Cited

U.S. PATENT DOCUMENTS

| | | |
|---|---|---|
| 3,592,203 A | 7/1971 | Johnson |
| 3,746,017 A | 7/1973 | Casselman |
| 3,881,502 A | 5/1975 | Bennington |
| 3,908,677 A | 9/1975 | Beach |
| 4,005,721 A | 2/1977 | Yasumoto |
| 4,008,728 A | 2/1977 | Sanchez |
| 4,016,892 A | 4/1977 | Chodorow |
| 4,151,851 A | 5/1979 | Bragg |
| 4,178,947 A | 12/1979 | McCourry et al. |
| 4,408,920 A | 10/1983 | Walther et al. |
| 4,508,125 A | 4/1985 | Loubier |
| 4,518,000 A | 5/1985 | Leverette |
| 4,548,219 A | 10/1985 | Newman et al. |
| 4,556,074 A * | 12/1985 | Morin et al. ................. 132/323 |

(Continued)

Primary Examiner—John J. Wilson
Assistant Examiner—Robyn Doan
(74) Attorney, Agent, or Firm—Knobbe, Martens, Olson & Bear, LLP

(57) ABSTRACT

A hand-held dental flossing device has a housing with a handle that may be held with one hand. A dental floss supply is located in the housing and a winding gear is rotatably mounted to the housing. A free end of the dental floss strand from the floss supply is threaded through the housing into a floss exit arm of the housing where it passes through an exit opening to an exposed area of the flossing arm. Used dental floss returns into the housing, via a receiving opening, where it passes through an optional disinfectant supply before or as it wound onto the winding gear. The housing has an opening where the winding gear extends therefrom and is accessible to the fingers of the user's hand. The winding gear has teeth that cooperate with a stopper to form a one-way ratchet gear. A floss-tensioning button is located in the housing and has first and second ends extending from the housing. The first and second ends are accessible to the user's hand holding the handle of the flossing device. When in a first position, the tensioning button allows the floss strand to be readily advanced by winding the gear while in a second position, the floss strand is relatively taut so that winding the gear will even further tension the strand. The device may have an F-shaped cross-section, enlarged, funnel-shaped openings for the floss to exit and enter the housing, and a disinfectant supply for disinfecting used floss. The device may be reloadable with floss.

18 Claims, 9 Drawing Sheets

U.S. PATENT DOCUMENTS

| | | |
|---|---|---|
| 4,574,823 A | 3/1986 | Uriss |
| 4,638,823 A | 1/1987 | Newman et al. |
| 4,638,824 A | 1/1987 | De La Hoz |
| 4,655,234 A | 4/1987 | Bowden |
| 4,660,584 A | 4/1987 | Wofford |
| 4,817,642 A | 4/1989 | Lipp |
| 4,881,560 A | 11/1989 | Blank et al. |
| 4,898,196 A | 2/1990 | Eason |
| 4,995,361 A | 2/1991 | Lorenzana et al. |
| 5,029,593 A | 7/1991 | Huttunen |
| 5,033,488 A | 7/1991 | Curtis et al. |
| 5,038,806 A | 8/1991 | Ewald |
| 5,040,554 A | 8/1991 | Rosenberger |
| 5,046,212 A | 9/1991 | O'Conke |
| 5,060,681 A | 10/1991 | Westbrook et al. |
| 5,063,948 A | 11/1991 | Lloyd |
| 5,085,236 A | 2/1992 | Odneal et al. |
| 5,105,840 A | 4/1992 | Giacopuzzi |
| 5,167,753 A | 12/1992 | McCullough et al. |
| 5,174,313 A | 12/1992 | Rosenberger |
| 5,209,251 A | 5/1993 | Curtis et al. |
| 5,220,932 A | 6/1993 | Blass |
| 5,226,435 A | 7/1993 | Suhonen et al. |
| 5,246,021 A | 9/1993 | Katz |
| 5,259,631 A | 11/1993 | Brands |
| 5,269,331 A | 12/1993 | Tanriverdi |
| 5,280,796 A | 1/1994 | Rosenberger |
| 5,280,797 A | 1/1994 | Fry |
| 5,284,169 A | 2/1994 | Gilligan et al. |
| 5,357,990 A | 10/1994 | Suhonen et al. |
| 5,375,614 A | 12/1994 | Navratil |
| 5,375,615 A | 12/1994 | Wahlstrom |
| 5,423,337 A | 6/1995 | Ahlert et al. |
| 5,495,863 A * | 3/1996 | Bergman .................... 132/326 |
| 5,505,216 A | 4/1996 | Gilligan et al. |
| RE35,439 E | 2/1997 | Rosenberger |
| D380,869 S | 7/1997 | Bergman |
| 5,650,035 A | 7/1997 | McGaha et al. |
| 5,678,580 A | 10/1997 | Sherman |
| 5,680,876 A | 10/1997 | Hasham et al. |
| 5,682,911 A | 11/1997 | Harada |
| 5,722,439 A | 3/1998 | Endelson |
| 5,765,576 A | 6/1998 | Dolan et al. |
| 5,787,907 A | 8/1998 | Endelson |
| 5,819,768 A | 10/1998 | Bible et al. |
| 5,857,471 A | 1/1999 | Harada |
| 5,875,797 A | 3/1999 | Chiang et al. |
| 5,878,759 A * | 3/1999 | Arias ........................ 132/325 |
| 5,896,867 A | 4/1999 | McGaha et al. |
| 5,937,874 A | 8/1999 | Guay et al. |
| 5,967,153 A | 10/1999 | Mitha et al. |
| 6,039,054 A | 3/2000 | Park et al. |
| 6,065,479 A | 5/2000 | Chodorow |
| 6,080,481 A | 6/2000 | Ochs et al. |
| 6,155,274 A | 12/2000 | Stein |
| 6,220,256 B1 | 4/2001 | Dolan et al. |
| 6,227,210 B1 | 5/2001 | Wyss |
| 6,253,774 B1 | 7/2001 | Mason |
| 2002/0145066 A1 | 10/2002 | Schweigert |
| 2002/0170570 A1 | 11/2002 | Bergman |

* cited by examiner

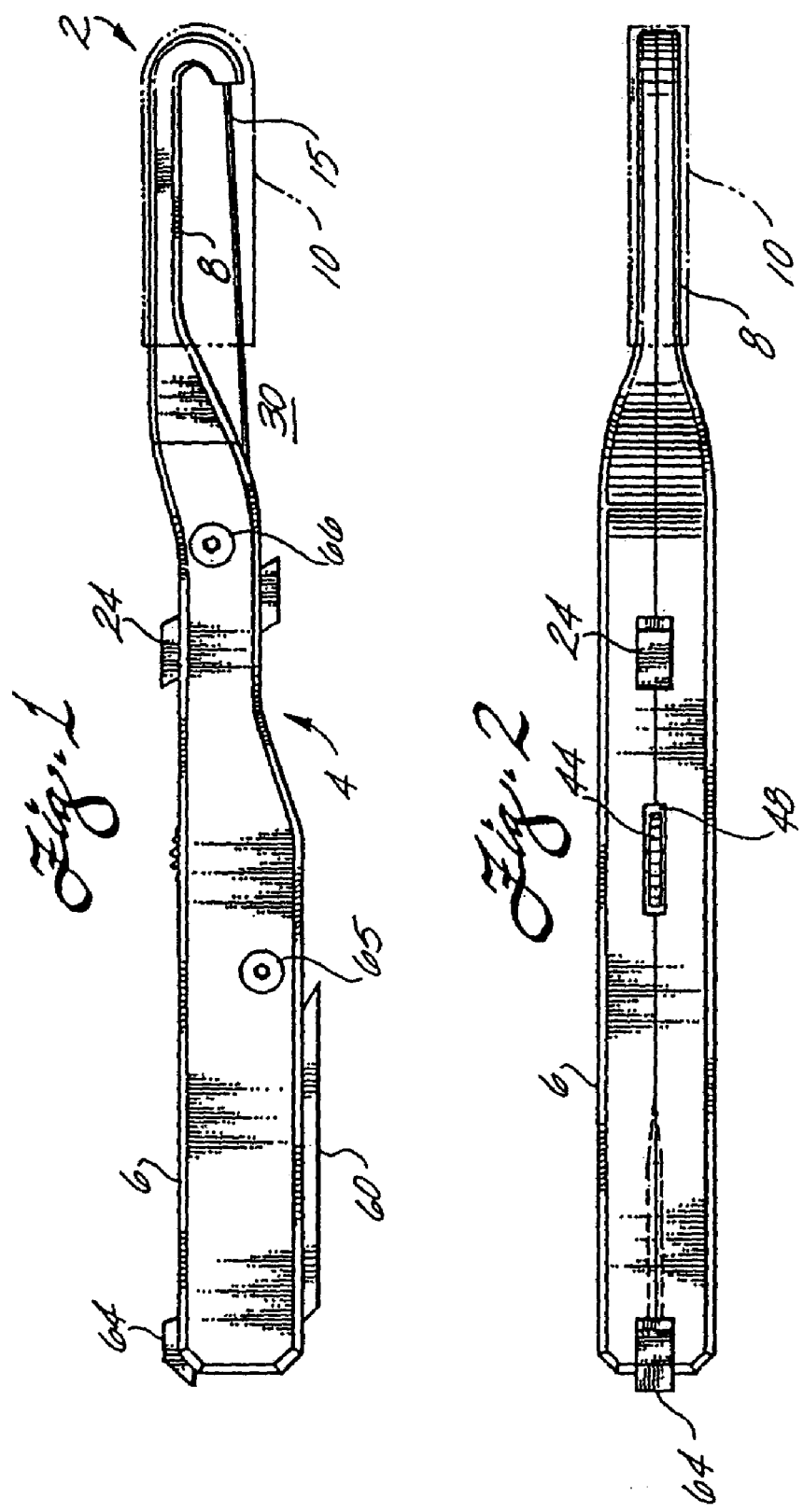

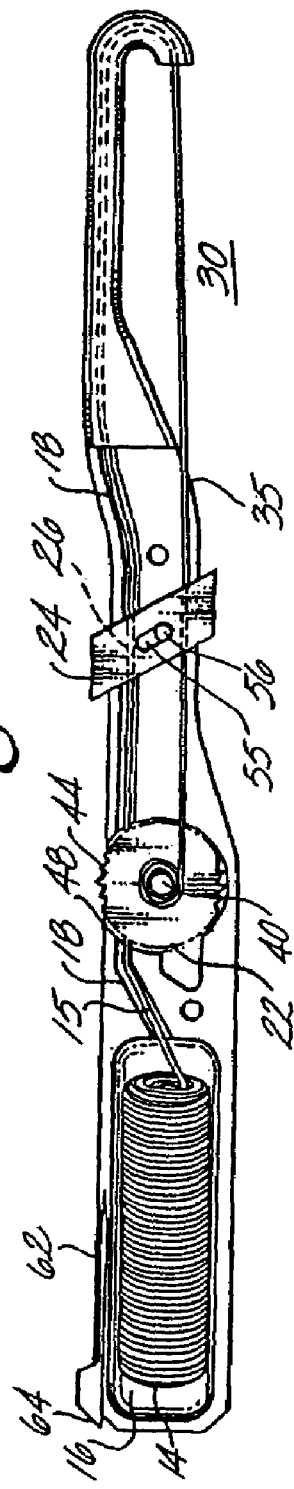
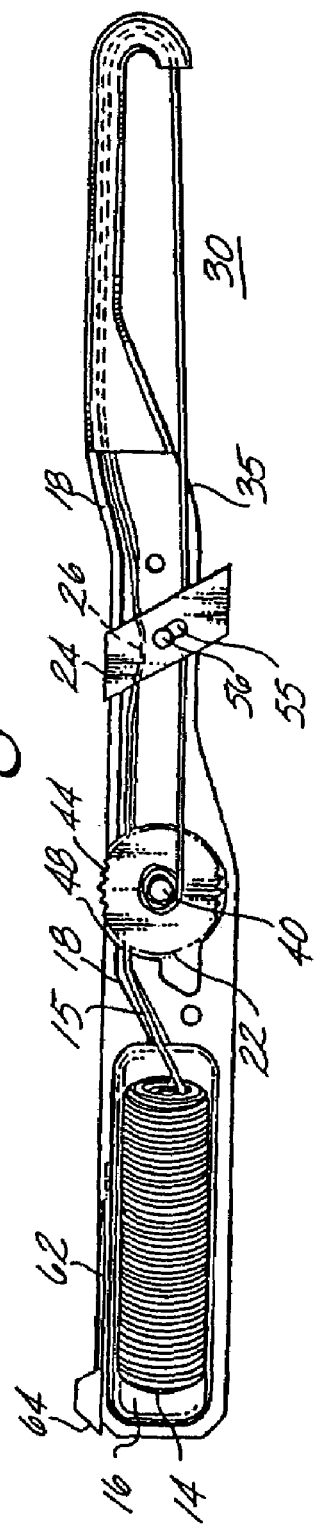

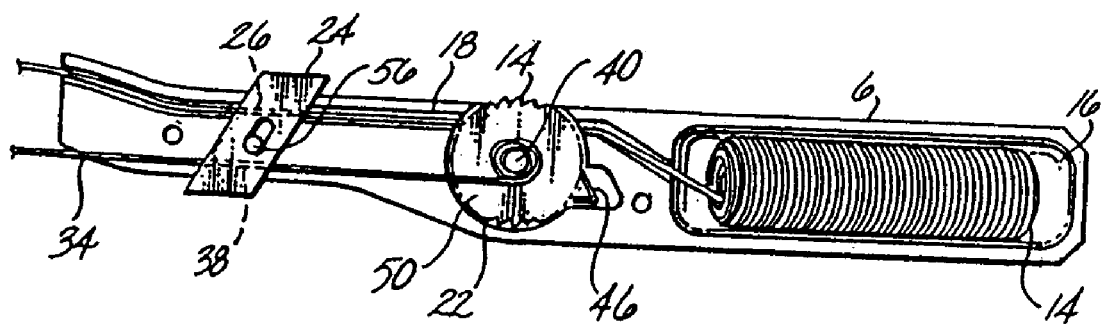

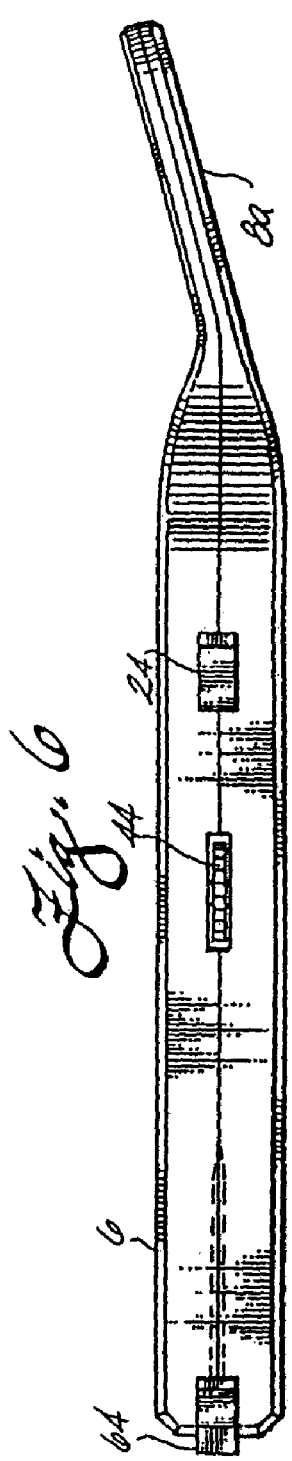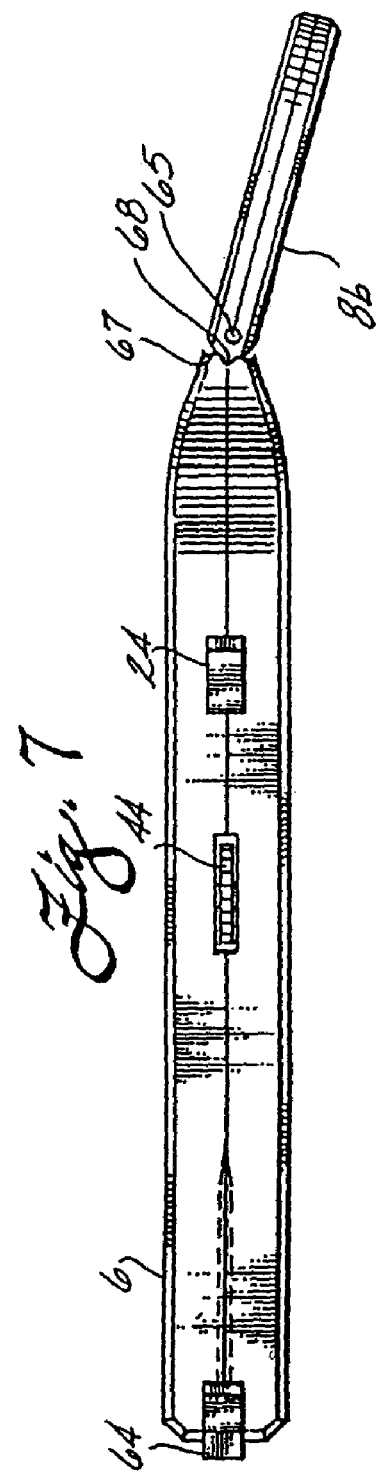

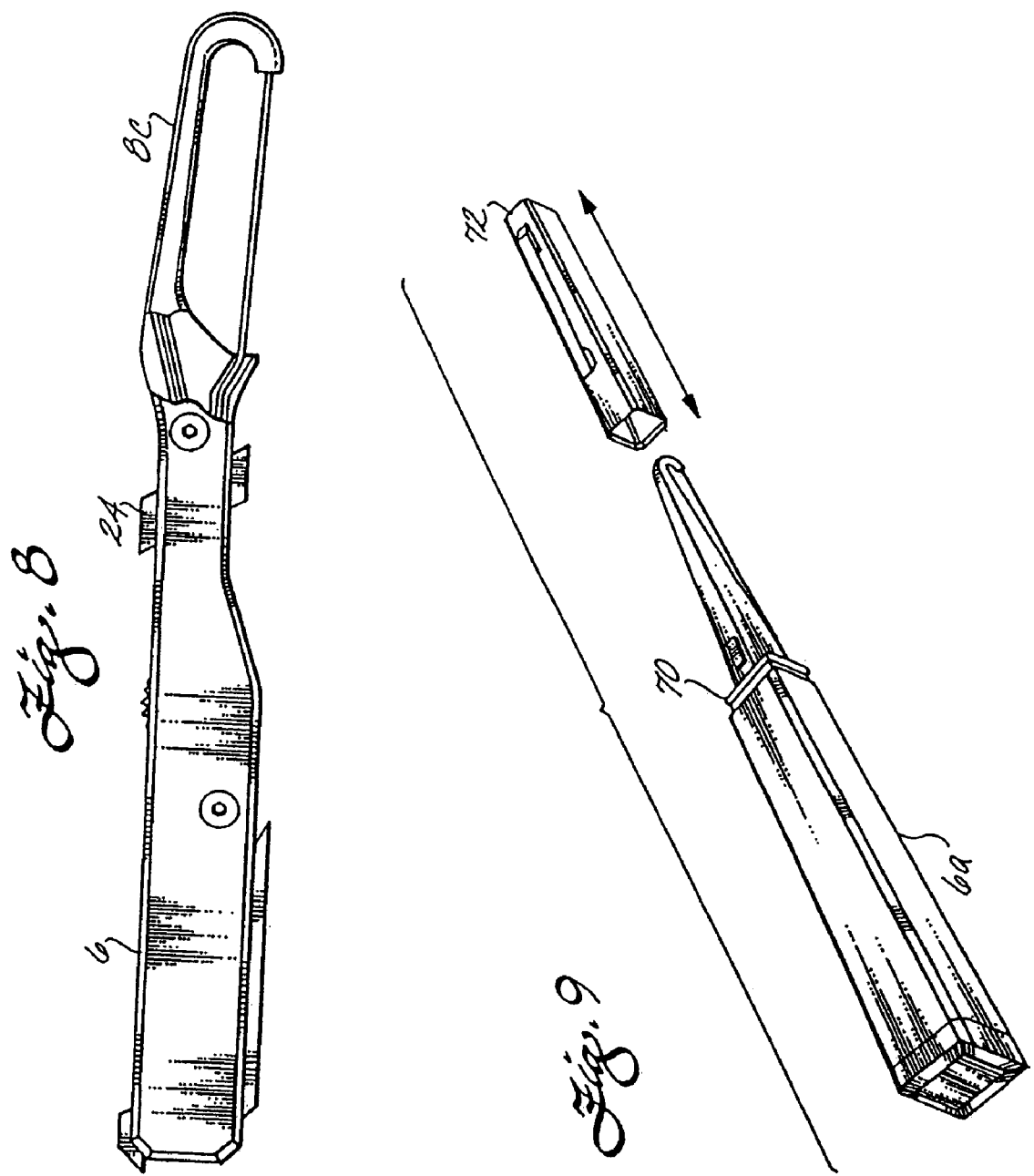

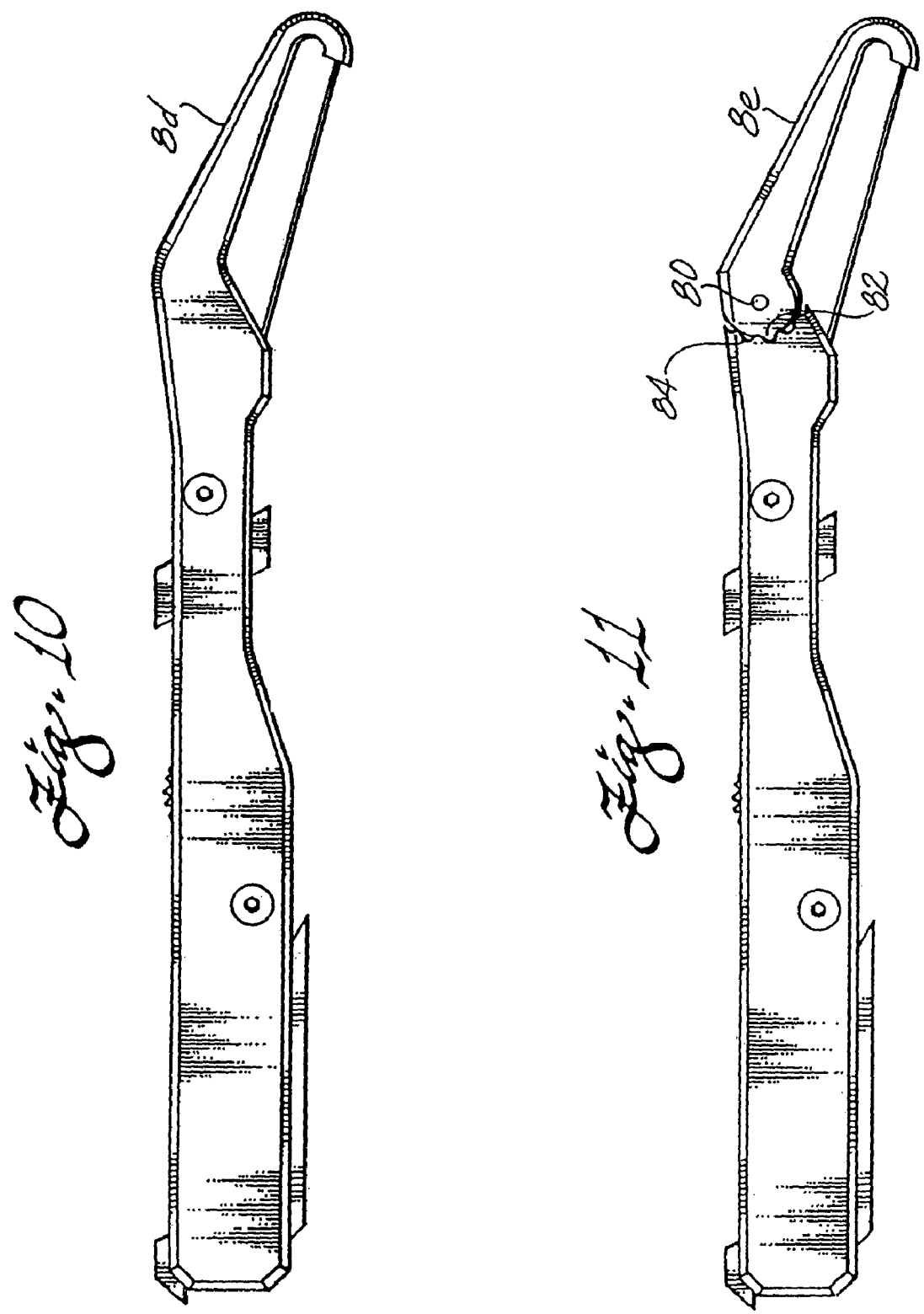

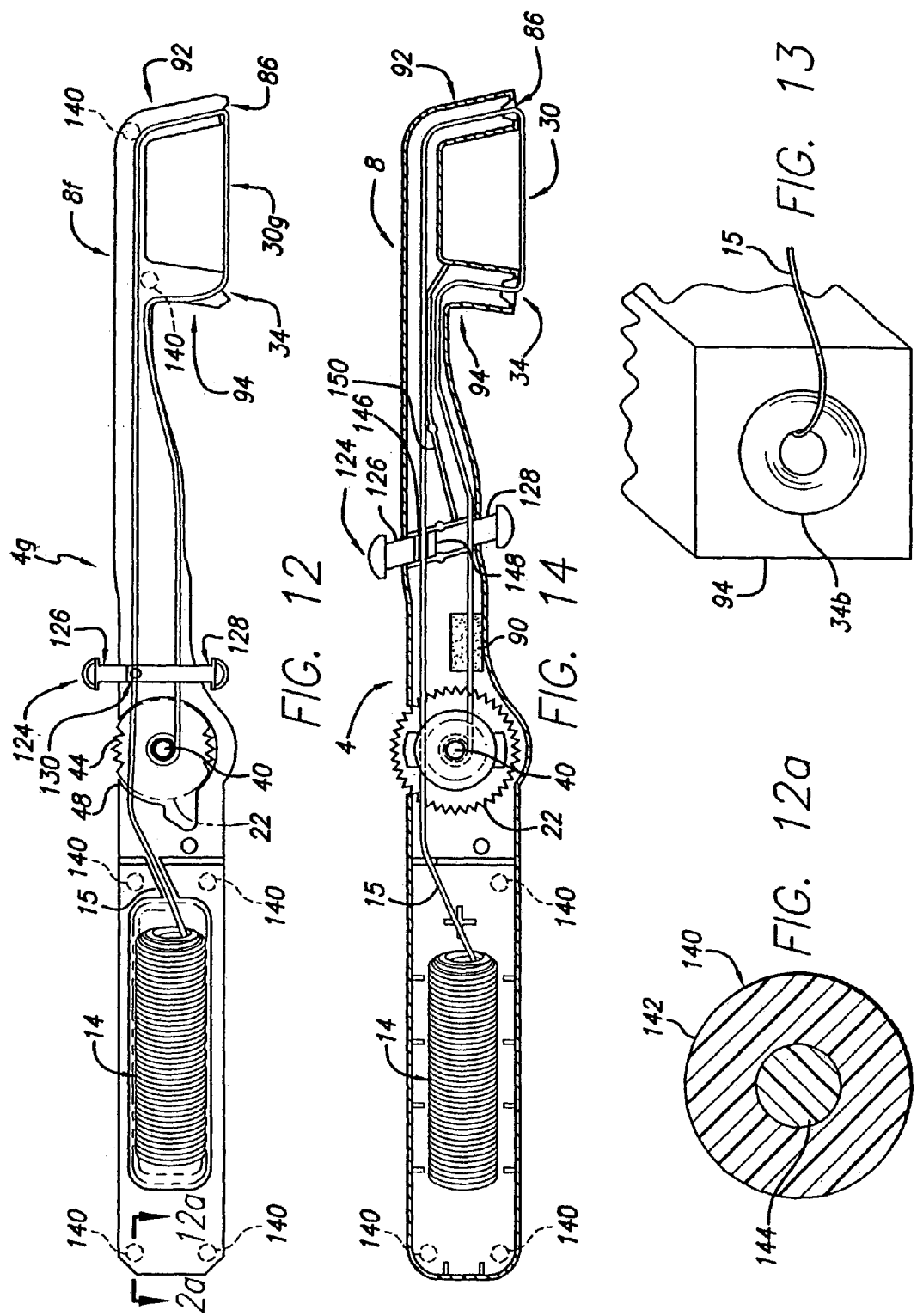

FLOSSING DEVICE WITH ADVANCING AND TENSIONING MECHANISM

RELATED APPLICATIONS

This application is a continuation of U.S. application Ser. No. 09/861,254, filed May 18, 2001, now U.S. Pat. No. 6,874,509 the entirety of which is hereby incorporated by reference.

This patent application is related to U.S. application Ser. No. 238,389, filed May 5, 1994, for FLOSSING DEVICE WITH ADVANCING AND TENSIONING MECHANISM, now U.S. Pat. No. 5,495,863; and to co-pending United States Patent Application titled DENTAL FLOSS WITH HIGH STRENGTH CORE AND WRAPPED SHEATH, filed Dec. 22, 2000, which are both incorporated herein by this reference.

BACKGROUND OF THE INVENTION

1. Field of the Invention

The present invention relates to a hand-held flossing device, which has a floss advancing mechanism and a simple-to-use tensioning mechanism for providing the floss with sufficient tension to be of practical use.

2. Description of the Related Art

Flossing regularly is important to dental health. However, flossing by holding the floss tightly between the user's two hands is cumbersome because it is hard to reach back teeth, and it is often hard to achieve sufficient tension without hurting one's hands. Moreover, it is not a sterile practice because the user's hands touch both fresh and used floss. To simplify flossing and avoid some of these problems, many flossing aids have been developed. In fact, an early flossing device is disclosed in U.S. Pat. No. 754,851 issued Mar. 15, 1904 to Bessonet, which provides for a manually threaded fork and a tensioning screw to tighten the floss when threaded. Because in this device the floss must be manually advanced and threaded, its use is cumbersome.

Another flosser is disclosed in U.S. Pat. No. 1,666,877 to Cummer, which issued in 1928. Cummer notes that floss holders have the problem of maintaining the floss taut as it can stretch during use. He uses a spring-loaded actuator arm to try to solve the problem. U.S. Pat. No. 3,746,017 to Casselman, issued in 1973, discloses a floss holder that includes a floss take-up reel for used floss. A new floss spool is insertable into and a used spool is removable from the device by means of a removable cover, which provides access to the spools. New floss is pulled from the supply spool, threaded through the device and wrapped onto a take-up reel. A slide is movable to a position where the supply reel can rotate freely so that floss can be advanced by rotating the take-up reel with the user's fingers. The slide is then moved to a position where the supply reel is locked in place and tension on the floss may be increased by further rotating the take-up reel, due to a spring ratchet system. A problem with this system is maintaining tension. In addition, new floss must be threaded onto or separately provided on a supply reel.

U.S. Pat. No. 5,060,681 to Westbrook, et al. discloses a flosser that includes a take-up reel actuated to advance floss by a user pressing forward and downwardly on an actuator knob, which has notches that engage and advance the take-up reel. To lock the reel, the user lets go of the knob which then retracts upwardly and rearwardly due to a spring bias, and locks the reel into place. The device is difficult to enhance the tension on the floss after the user releases the knob.

Yet another flosser is disclosed in U.S. Pat. No. 5,269,331 to Tanriverdi issued in 1993. It has supply and take-up reels. The floss is advanced by manually advancing the take-up reel. A locking member prevents any rotation of the supply reel independent of the take-up reel. The take-up reel is rotated to feed new floss by manual advancement. Tension may be provided by pressing and holding down a bulged portion of the case where the supply reel is located.

Other flosser devices are disclosed in the following U.S. Pat. Nos. 4,790,336; 5,038,806; 5,105,840; 4,660,584; 4,898,196; 5,029,593; 4,005,721; 4,817,642; 3,881,502; 3,592,203; 4,518,000; 4,151,851; 4,178,947; 4,008,728; 3,908,677; and 4,508,152.

What is needed is a flossing device that is simple to use in that it is easy to advance floss and easy to provide enhanced tension to enable one to floss. What is also needed is a flossing device which is easy to hold, safe to use, separates the new and used floss, is easy to manufacture and is compact.

SUMMARY OF THE INVENTION

In one embodiment, the present invention provides a hand-held flossing device including a housing, preferably of plastic, which is generally toothbrush-shaped. The housing has a compartment for new floss, and a separate area for used floss. In a preferred embodiment, there is a disinfectant supply comprising a germicide, antiseptic, anti-microbial, or similar disinfecting composition for the used floss. The housing is preferably openable to permit the user to replace a used spool with a new spool of floss; or a used disinfectant supply with a new disinfectant supply. A winding reel is rotatably attached to the housing and the free end of the floss is attached to the reel so that when the wheel is rotated, the floss will unwind from the new floss spool. Used floss may pass through the disinfectant supply and then wrap around the winding reel. The reel preferably is combined with a winding gear and extends outside the housing so that it can be advanced by the thumb or fingers of the user to advance the floss. A one-way catch allows the winding gear to ratchet.

The housing has a handle area and an arm extending from the handle area. The extending arm preferably has an F-shaped profile and comprises a floss exit arm and a floss entrance arm. A tension knob or trigger is located on or in the housing. New floss passes from the spool through the tension trigger, through the floss exit arm of the extension arm and past an open area where the floss is exposed. The floss then returns into the housing through a receiving opening in the floss entrance arm and passes through an optional disinfectant supply. The floss then preferably attaches to the winding reel. The floss is advanced by winding the reel. The ratchet action of the reel with the one-way catch prevents loosening of the floss. To tension the floss even more, the tension knob is pressed which pinches the floss to inhibit new floss from being pulled from the spool and also enhances the tension. Further tension may be applied to the floss by winding the take-up reel even more.

In a preferred embodiment, the knob is compression fit or friction fit into the housing and has a slot through which a pin connected to the housing passes. The handle is tapered and the housing is pen or pocketsize. A new floss spool is preferably coreless, i.e., it does not require a supply reel. The generally F-shaped profile of the extension arm provides better tensioning, by making the exposed length of floss shorter, and also provides improved maneuverability. There is a receiving opening in the floss entrance arm, and it preferably has a generally elongated, conical (i.e., funnel) shape to provide reduced friction on the floss. A conical shaped receiving opening facilitates re-entry into the housing of used floss that may have been shredded in use and assists the threading process during manufacturing or any rethreading, but any appropriate shape may also be used.

Alternately, the receiving opening may be enlarged to facilitate re-entry and threading of the dental floss strand. For example, width $W_1$ of the receiving opening may be substantially larger than the width, $W_2$, of the dental floss strand. Preferably, an exit opening in the floss exit arm is also generally either enlarged, elongated, or funnel-shaped to facilitate the threading process and advancement of the floss strand to the exposed area. The generally enlarged, funnel or elongated shape of the exit and/or receiving openings additionally prevents the edges of the openings from biting into the floss during ratcheting. Alternately, the receiving opening and/or exit opening may contain a roller mechanism to aid in the threading process and to pack the floss before it passes into, or out of, the respective opening.

A disinfectant supply comprising an anti-microbial, germicidal, antiseptic, anti-bacterial, or similar composition is optionally provided inside the flosser to apply a germicide, or similar disinfecting composition, to the used floss. If there is a disinfectant supply, used floss entering the housing through the receiving opening in the floss entrance arm preferably passes through the disinfectant supply and is "wiped" with germicide as the used floss is wound onto the winding reel. The disinfectant supply is especially advantageous in embodiments where the device is openable and the user removes and replaces the used floss.

The floss in the supply spool is found, oval, or eccentric, and is internally wound which facilitates operation of the invention. The device preferably has a pocket clip and a toothpick or a plaque pick is removably inserted into the device housing for convenience. The device may be provided with a cover, which fits over the tapered housing at the F-shaped or J-shaped extension arm to improve appearance and to provide protection for the exposed portion of the floss during storage. The device may be disposable or nondisposable with the new spool compartment of the device being openable to insert another spool and the winding reel being accessible to attach the end of the new spool.

The device is easy to hold. The simplicity of construction of the device and the ability to easily enhance tension promotes use of the device to stop tooth decay. In fact, the device is constructed so that it is easy for all to use regardless of age or ability, including the elderly who may have arthritis or the very young who may lack coordination. Moreover, the device provides a disinfecting agent and maintains separate sections for new and used floss to help prevent the spread of germs. It is quite useful for those with gum and mouth diseases and may even have application with HIV-positive persons.

BRIEF DESCRIPTION OF THE DRAWINGS

These and other advantages, features and aspects of the preferred embodiment of the invention may be more apparent with reference to the detailed description to be read in conjunction with the drawings, in which:

FIG. 1 is a side view of a first embodiment of a flosser according to the invention;

FIG. 2 is a top view of the flosser of FIG. 1 with its cover on;

FIG. 3 is a side view of the flosser with its side open to show internal components;

FIG. 4 is a view similar to FIG. 3 with a tensioning knob in the actuated position;

FIG. 5 is a partial view of the other side of the flosser with its side open to show the other side of the internal components;

FIG. 6 is a top view of a flosser having an extension arm bent to the left when looking down according to a second embodiment of the invention;

FIG. 7 is a top view of a flosser having a extension arm bent to the right when looking down according to a third embodiment of the invention and in which the extension arm is pivotable left and right;

FIG. 8 is a side view of a flosser bent downward according to a fourth embodiment of the invention;

FIG. 9 is an enlarged perspective view of a flosser according to a fifth embodiment of the invention;

FIG. 10 is a side view of a sixth embodiment of the invention, where the extension arm is bent downward;

FIG. 11 is a side view of a seventh embodiment of the invention where the extension arm is pivotable up and down;

FIG. 12 is a side view of an eighth embodiment of the invention where the extension arm has an F-shape and where the receiving opening is generally funnel-shaped;

FIG. 12a is an enlarged sectional view taken along a line 12a—12a of FIG. 12;

FIG. 13 is an enlarged perspective view of the receiving opening of FIG. 12;

FIG. 14 is a side view of a ninth embodiment of the invention where the flosser comprises a disinfectant supply and where the receiving opening is generally funnel-shaped.

DETAILED DESCRIPTION OF THE PREFERRED EMBODIMENT

Figure 15A:
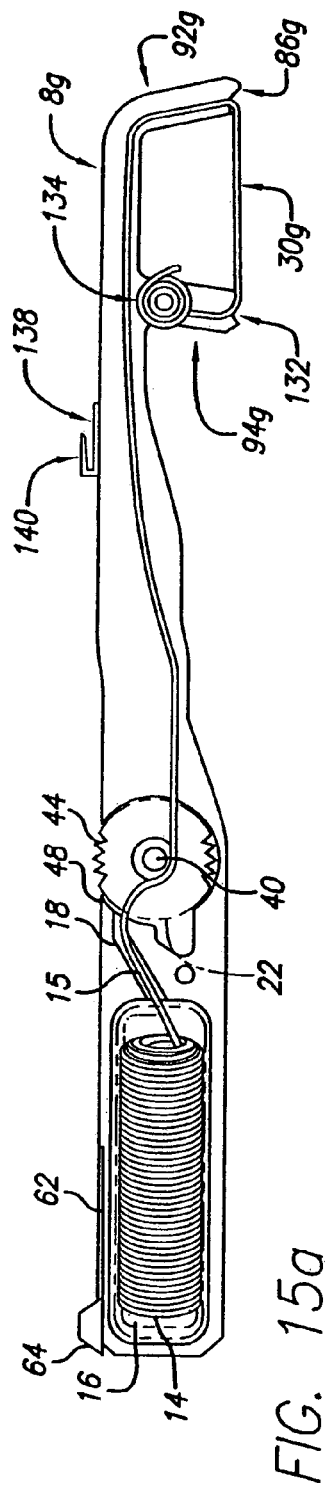
FIGS. 15a and 15b are side views of a tenth embodiment of the invention having an F-shaped extension arm where floss from the exposed area fits into a groove on the entrance arm and is wound around a knob.

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

In general, a flossing device according to the invention in a preferred embodiment has an easy-to-use tensioning or locking button to increase the tension on the floss. In one embodiment of the invention, as shown in FIGS. 1–5, a flosser 2 has a generally elongated housing 4 including a handle 6 and an extension arm 8. Preferably, the device is shaped so that it may be held like a toothbrush. There is a cover 10, which is fit over the extension arm 8 and may be held thereon by a friction fit.

A spool 14 of floss 15 fits in a compartment 16 of the flosser. The floss spool is preferably round, oval, or eccentric and is internally wound. An eccentric shape, such as substantially rectangular, allows one to maximize the amount of floss supply to fit whatever design and shape exists for compartment 16 which, in turn, may be dictated by the handle design and shape. Internal winding enables the free end of the floss to be at the inside of the spool so that a winding reel for the floss supply is not needed, although one could be used where externally winding the floss is desired.

The floss passes out of compartment 16 through a channel 18 past one side of a winding gear 22 and on through a tensioning button 24 having an aperture 26 through which the floss passes. The floss continues on through channel 18 into the extension arm 8, which is preferably generally J-shaped or F-shaped (and/or bent J- or F-shaped or pivotable J- or F-shaped). The floss 15 exits the J- or F-shape to an exposed area 30 and returns into the housing at a receiving opening 34 and passes through tensioning button 24 at an aperture 38. The floss then passes to the winding gear 22 where it is fixed to an axle 40 (or winding reel) on an opposite side of the gear as the floss when coming from spool 14. The axle 40 (winding reel) is fixed to the gear so that rotation of the gear rotates the axle to wind the floss around the axle and at the same tine advance floss from spool 14. Gear 22 has serrations 44 on its periphery which mesh with a ratchet arm 46 (FIG. 5), such as a spring clip. The ratchet arm and serrations cooperate so that the winding gear rotates only in one direction to pull floss from spool 14. The winding gear may be advanced by a user holding handle 6 by pulling or pushing on an exposed portion of winding gear 22 proximate an opening 48 in the top of the housing. Whether the gear will be pulled or pushed depends on which way the serrations and ratchet allow the gear to be wound. The portion of the floss wound on axle 40 is isolated in another compartment 50 on the side of the gear 22 where the floss is attached to axle 40. The axle 40 is rotatable with respect to the housing.

In the past, it has been difficult to achieve sufficient tension on the floss to perform flossing. Even where sufficient tension could be obtained, the mechanism to obtain it would be quite complex. In the invention, the single tensioning button 24 is used. It is preferably press fit into a channel in the housing and is normally kept in a first, low tension position (e.g., FIG. 3) where the floss in channel 18 and the return floss pass substantially straight through the button. After the user winds the floss to obtain fresh floss in the exposed area 30, the fresh floss may be further tensioned by pressing button 24 so that the floss passing though the button 24 becomes out of alignment with the floss in channel 18 to lengthen the path of the floss and mainly to pinch it between the button and the housing, and thereby enhance the tension thereon. (A horizontally slidable tensioning button which uses the same type of pinching action may be used in place of a vertically movable button.) This pinching also inhibits advancing the floss from spool 14. Accordingly, to further enhance the tension, the winding-gear 22 may be further wound, which will tighten the floss from the nearest point, i.e., where it exits the aperture 26 of the tension button 24 to the point where it attaches to axle 40.

The floss supply spool is, in effect, locked off by the tension button pinching the floss between it and the housing. The floss which returns through button 24 to axle 40 passes through a wide channel or no channel such that it will not be pinched by movement of the button. Accordingly, the tension of the floss in the exposed area 30 is further enhanced by ratchet action. The user then flosses until the exposed floss is spent. Then the user may further advance the floss by moving the tensioning button back to the first position and by further winding gear 22. The user will then move the tensioning button back to the second position and enhance the tension as needed for additional flossing. As can be seen from the drawings, the operation of holding the flosser 2, advancing the floss using winding gear 22 and further tensioning the floss using the tension button 24 can all be performed with one hand. The tension button 24 can be pushed from the top or bottom of the flossing device and so it is very simple to tension or release the floss.

As shown in FIGS. 1–5, tensioning button 24 has an elongated hole 55 through which a pin 56 fixed to the housing 4 passes. The pin defines the limits of motion of the tensioning button so that the button will stay connected to the housing and so that the first and second positions of the button are defined.

The underside of handle 6 of the housing can have a pocket clip 60 attached to it similar to a pocket clip on a pen. The housing may also have a slot 62 defined in it for receiving a plaque pick 64 similar to a plaque or toothpick in a pocketknife. Housing 4 is preferably injection-molded in left and right halves. The halves may be fixed together by known means, such as screws 59, 66, glue, epoxy or by a sonic weld process. The flosser may be constructed to be disposable when the floss is used up or in such a way that the floss compartment 16 can be exposed and the rest of the floss path so that the old floss can be removed and a new floss spool can be inserted in the compartment with sufficient floss to be threaded to the rest of the device and attached to axle 40 at its free end, e.g., by means of a monofilament leader at the free end.

The handle preferably tapers so that the handle can be sufficiently thick to readily hold while the extension arm or flossing arm is sufficiently thin to be easy to maneuver within the user's mouth. An extension arm having a J-shape instead of two V-shaped prongs avoids sharp, exposed edges and is also easier to use in that the device may be held and used like a toothbrush. Yet, preferably, the extension arm is generally F-shaped, which further facilitates use and operation of the device by making the exposed length of floss shorter and providing better tension.

Alternative embodiments are shown in FIGS. 6–10 as follows:

FIG. 6 is the top view of a flosser substantially the same as the flosser of FIGS. 1–5, except that the extension or flossing arm 8a is bent to the left, and FIG. 7 is the same as the flosser of FIGS. 1–5, except that the extension arm 8b is bent to the right. These embodiments may be easier for certain people to use to get at molars or wisdom teeth. This arm 8b is pivotable left and right about a pin 65 (internally connected to handle 6), and is held at a desired angle by a detent mechanism, including detent surface 67 of the handle and a projection 68 of the arm 8b. The embodiment of FIG. 8 is also the same as that of FIGS. 1–5, but it has a handle 6a and slight downward bend of the flossing arm 8c, which may make it easier for some users to reach different teeth. For the embodiment of FIG. 8, a suitable cover can be designed. Obviously, any embodiment may be made with a suitable cover.

The embodiment of FIG. 9 shows a pocket-size version of the device which has the same components as that of FIGS. 1–5, but has a handle 6b and a square-shaped cross section and has a detent mechanism 70 to hold its cover 72. There may also be a plaque pick and clip in this version. The spool in this version is longer and narrower, similar to the models shown in FIGS. 10 and 11. However, the differences between the model of FIGS. 10 and 11 are that FIG. 10 has a substantially angled extension arm 8d, while FIG. 11 has an up and down, pivotable extension arm 8e. The extension arm of FIG. 11 is journaled to the rest of the housing about a pivot pin 80 and is held in place at the selected angle by means of tension detents 84 on the handle and a projection 82 on the extension arm similar to the side-to-side pivotable system of FIG. 7.

The embodiment of FIG. 12 shows a device having the same components as that of FIGS. 1–5, but having a generally F-shaped extension arm 8f including an exit opening 86 in the floss exit arm 92 and a receiving opening 34 in the floss entrance arm 94. The exit opening 86 and receiving opening 34 preferably have an enlarged, funnel (cone with the frustrum missing) or elongated shape to reduce friction on the floss. The shape of the opening provides improved advancement of the floss 15, and smooth re-entry of used floss into the housing 4g and aids in manufacture by simplifying the threading process. A locking and tensioning button 124 is preferably friction fit into a channel in the housing 4g. The tensioning button 124 has first and second ends 126, 128 that define the limits of motion of the tensioning button 124, so that it slides between an unlocked, or low tension, position and a locked, or high tension, position.

As shown in FIG. 12, the tensioning button 124 is halfway between the unlocked and locked positions. In the unlocked position (lower position of the button), used floss passes substantially straight through an aperture 130 in the tensioning button 124. After the user winds the floss to obtain fresh floss in the exposed-area 30g, the fresh floss may be further tensioned by pushing end 128 upward so that the used floss passing though the tensioning button 124 is pinched, e.g., between the upper portion of the housing and the hole in the button, thereby enhancing the tension thereon. (A horizontally slidable tensioning button that uses the same type of pinching action may be used in place of a vertically movable button.) This pinching also inhibits advancing the floss from spool 14. Accordingly, to further enhance the tension, the winding gear 22 may be further wound. Other means of pinching the floss or otherwise fixing it at the button may be used, such as a clamp responsive to motion of the button.

FIG. 13 is an enlarged perspective view of the receiving opening 34b and entrance arm 94. The outer edge of the receiving opening 34b may be rounded to further reduce friction on the floss 15.

FIG. 14 shows a device that may also comprise a generally F-shaped extension arm 8 including an exit opening 86 in the floss exit arm 92, and a receiving opening 34 in the floss entrance arm 94. The embodiment shown in FIG. 14 may additionally comprise a disinfectant supply 90. A locking and tensioning button 124 is preferably friction fit into, or shaped to sit in, a channel in the housing 4. The tensioning button 124 has first and second ends 126, 128 that define the limits of motion of the tensioning button 124, so that it slides between an unlocked, or low tension, position and a locked, or high tension, position. The tensioning button of the embodiment shown in FIG. 14 also comprises a groove or channel 146, which is preferably disposed slightly above the center point 148 of the tensioning button 124.

The floss 15 from the floss supply 14 sits in the groove 146 in the tensioning button 124, and is separated from the bottom half of the flossing arm by a ridge or septum 150 that divides the top and bottom portions of the flossing arm 8. In the unlocked position, floss 15 glides substantially straight through groove 146 in the tensioning button 124. The user may then advance fresh floss 15 from the floss supply 14, through the F-shaped portion of the flosser arm 8, through opening 86, and to exposed area 30 by turning winding gear 22. To lock the tensioning button 124, the first end 126 is pushed downward so that the floss 15 sitting in groove 146 is displaced downward, thereby enhancing the tension thereon. (A horizontally slidable tensioning button that uses the same type of displacing action may be used in place of a vertically movable button.). Alternately, the flosser may be configured so that the bottom end 128 is pushed upward in order to lock the tensioning button 124. To further enhance the tension of the floss 15 in exposed area 30, the winding gear 22 may be further wound. Used floss returning to the housing 4 from the exposed area 30 is separated from the top portion of the flossing arm 8 by the septum 150 and is wound onto the axle 40 as fresh floss 15 is advanced to the exposed area 30 by turning winding gear 22 with the tensioning button 124 in the unlocked position. If the flosser comprises a disinfectant supply 90, the used floss 15 preferably passes through, or is wiped by, the disinfectant supply as it passes through the housing 4 to axle 40.

Figure 15B:
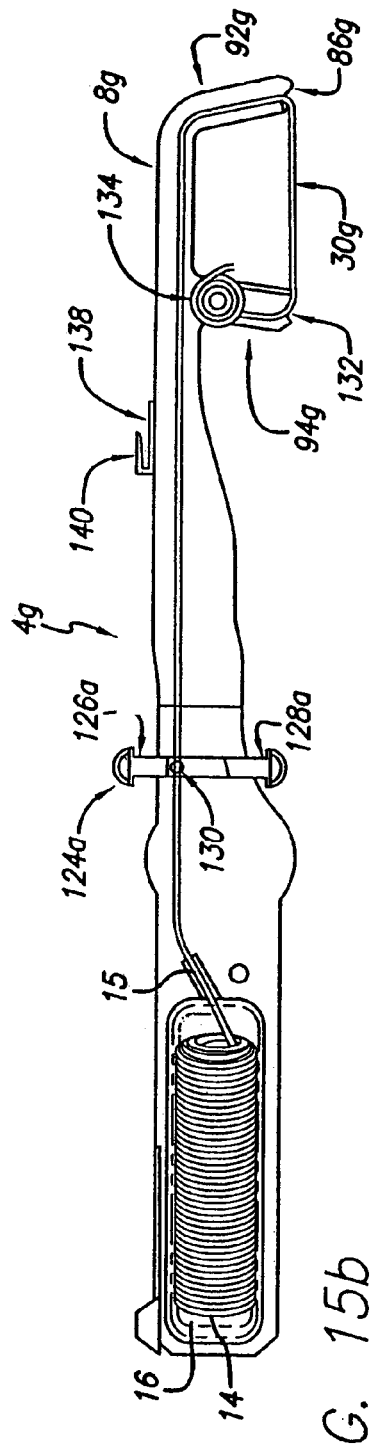

FIGS. 15a and 15b illustrate another embodiment of the invention having F-shaped extension arm 8g including exit opening 86g in the floss exit arm 92g, and a receiving groove or notch 132 in the floss entrance arm 94g. In this embodiment, a fresh floss supply path may be configured as in any of the previously described embodiments so that fresh floss is guided to the exposed area 30g.

In the embodiment of 15a, a winding gear 22 is disposed along the supply line. Fresh floss exits through, opening 86g in the floss exit arm 92g to the exposed area and is fit into a groove or notch 132. A portion of the floss is then wound around a button or knob 134 disposed on the external surface of the housing 4g, preferably near the notch 132. The button or knob 134 may be disposed on the right, left, or both sides of the housing so that right or left-handed users can easily use the device. A plate or protrusion 138 having a raised portion 140 with sharp edges is disposed near the knob 134 and can be used to cut off used floss. The plate 138 may be comprised of materials, including but not limited to, aluminum, stainless steel and plastic. Once the end of the floss 15 is wound around knob 143, fresh floss in, the exposed area 30g can be further tensioned by rotating the winding gear 22.

The operation of further tensioning the floss in the exposed area 30g can be performed with one hand. For example, the winding gear 22 may be positioned on the top or bottom of the housing and rotated with the thumb while holding the device in one hand. In addition, or alternatively, the embodiment of FIG. 15a may include a tensioning button 124a to tension the floss in the exposed area (FIG. 15b). The tensioning button 124a works in essentially the same manner as the tensioning button of FIG. 12. Once the floss 15 is wound around knob 134, the floss 15 in the exposed area 30g may be further tensioned by pushing ends 126a or 128a on tensioning button 124a. If a winding gear is also included, the winding gear 22 may be rotated (clockwise in FIG. 15a) after pushing ends 126a or 128a to further enhance tension of the floss 15 in the exposed area 30g. A pawl (not shown) or ratchet arm (e.g., as shown in FIGS. 1–5) may engage the gear to prevent counterclockwise rotation. New floss may be threaded by disengaging the pawl so that the floss will freely feed.

Figure 16:
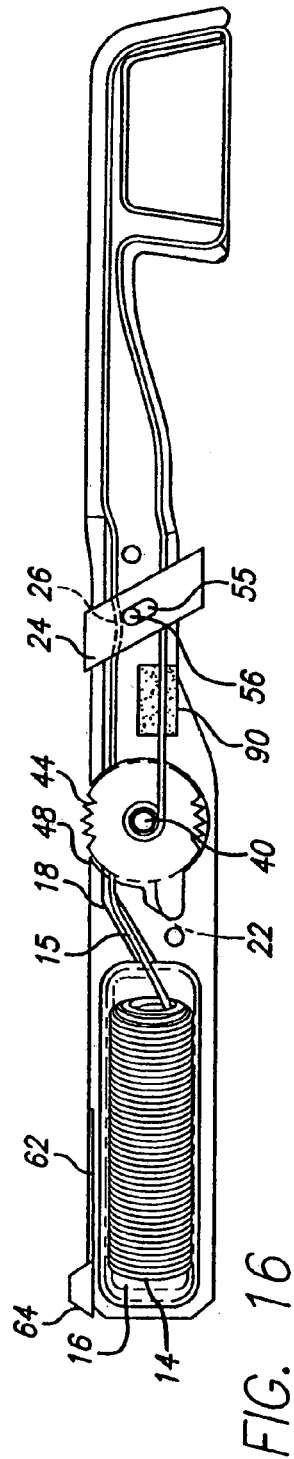
FIG. 16 is a side view of the flosser and disinfectant supply according to an eleventh embodiment of the invention.

The embodiments of FIGS. 1–15 may also include a disinfectant supply 90 (FIG. 16) to disinfect used floss. The disinfectant supply includes an anti-microbial, anti-septic, anti-bacterial, germicidal, or similar composition, and also helps prevent contamination of fresh floss. In the embodiments of FIGS. 1–15, floss returning into the housing through receiving opening 34 passes through the disinfecting supply 90 before it is wound onto the winding gear 22, the floss being wiped with disinfectant. In the embodiment of FIGS. 15a and 15b, a disinfectant supply may be located in extension arm 8g, but is preferably located in entrance arm 94g and in contact with groove 132, so that used floss is wiped with disinfectant as it passes in groove 132.

In all of the embodiments, the device may be reusable by making the floss supply spool re-loadable, and the winding gear rewindable (to remove used floss and to lock new floss into it, e.g., by putting a slot in the axle 40 (winding reel or just the friction of wrapping some hew floss). A hinged door, slidable plate with tabs (like a battery compartment cover), or other openable and closable structure may be provided in the housing for access to the spool area to insert a new spool, and to the winding reel to remove the used floss. Alternatively, for example, instead of permanently attaching the two housing halves, these could be snap-fitted together so that they may be unsnapped. This would simplify rethreading the new floss along the supply path. FIGS. 12 and 12a show an example of a rethreadable device where the housing halves snap-fit together by a snap-fit mechanism 140 at various locations of the housing 4. Each mechanism 140 includes a pin 144 projecting from one housing half and a ring 142 in the other housing half (FIG. 12a). The pin 144 friction fits inside the ring 142.

A winding reel could also extend externally of the housing 4 and thus the used floss can be readily removed and the new floss readily wound thereon. The supplied floss may also be externally located with respect to the housing 4. Accordingly, the floss can be externally secured and/or externally windable.

Figure 17:
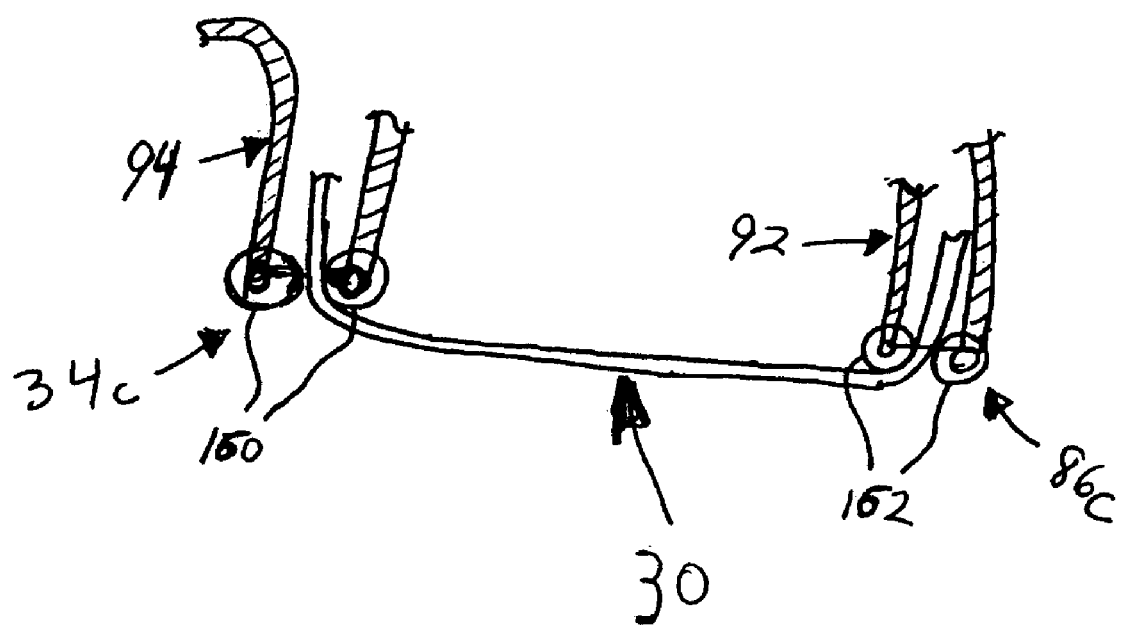
FIG. 17 is an enlarged partial sectional view of an exit and entrance opening and exposed floss in an eleventh embodiment of the invention where a roller mechanism is used at the entrance and exit.

FIG. 17 shows another embodiment of the invention where the floss 30 leaves exit arm 92 at an exit opening 86c having a roller mechanism 162, passes the exposed flossing area, and enters entrance arm 94 at a receiving opening 34c through a roller mechanism 160. Thus the receiving opening and exit opening contain roller mechanisms to aid in the threading process and to pack the floss before it passes into, or out of, the respective opening.

Modifications and improvements of the present invention will be apparent to those skilled in the art. For example, the tensioning button may have first and second ends protruding from the sides of the housing rather than the top and the bottom of the housing. The invention is not limited to the disclosed embodiments but is defined by the appended claims.

What is claimed is:

1. A hand-held flossing device, comprising:
   a housing having a handle and a head, the head having a top and a bottom;
   a dental floss supply disposed within the handle;
   a winding gear rotatably mounted within the handle and configured to securely hold a free end of the dental floss supply, the winding gear having at least a portion accessible from outside of the housing;
   a first elongate tine and a second elongate tine extending downwardly from the bottom of the head, the tines diverging relative to one another as they extend downwardly;
   an exit aperture formed in the first tine and an entrance aperture formed in the second tine;
   a floss path extending from the dental floss supply, through the handle, through the first tine and out the exit aperture, into the entrance aperture, through the second tine, and to the winding gear, the winding gear configured to advance floss along the floss path; and
   a lock disposed along the floss path and moveable between a locked position and an unlocked position to selectively inhibit the advancement of floss along the floss path;
   wherein a supply path is defined from the lock to the first tine, and a return path is defined from the second tine to the winding gear, and a septum separates at least a portion of the supply path from the return path so that the supply and return paths generally diverge from each other from the head toward the handle.

2. The hand-held flossing device of claim 1, wherein a length of each of the first and second tines is less than a length of the floss extending between the exit aperture and the entrance aperture.

3. The hand-held flossing device of claim 1, wherein rotation of the winding gear tensions the floss extending between the exit aperture and the entrance aperture.

4. The hand-held flossing device of claim 1, wherein the entrance aperture and/or exit aperture is tapered.

5. The hand-held flossing device of claim 1, wherein the housing is configured to allow a user to replace the floss supply with a new floss supply.

6. The hand-held flossing device of claim 1, wherein the lock is slidable between an engaged position and a disengaged position, the lock having a passage formed therethrough.

7. The hand-held flossing device of claim 6, further comprising one or more grooves formed within the housing that substantially align with the lock passage when the lock is in the disengaged position.

8. The hand-held flossing device of claim 7, wherein the floss passes through the lock passage, and tracks through the one or more grooves of the housing.

9. The hand-held flossing device of claim 8, wherein the one or more grooves are out of alignment with the lock passage when the lock is in the engaged position, thereby inhibiting subsequent advancement of the floss through the passage.

10. The hand-held flossing device of claim 1, wherein the supply path is generally adjacent the top and the return path is generally adjacent the bottom.

11. The hand-held flossing device of claim 10, wherein the housing comprises a floss supply compartment generally enclosing the floss supply, and a floss supply guide directs floss out of the compartment and toward the top of the housing.

12. A hand-held flossing device, comprising:
   a housing having a top, a bottom, opposing sides, a handle portion, a head portion, and a transition portion between the handle and head portions, the transition portion tapering toward the head portion so that a minimum distance between the top and bottom in the head portion is less than a minimum distance between the top and bottom in the handle portion;
   a first elongate tine and a second elongate tine extending from the bottom of the head portion, the first tine extending in a direction downwardly and away from the handle portion, the second tine extending in a direction downwardly and toward the handle portion so that the tines diverge from one another;
   a first aperture formed in the first tine and a second aperture formed in the second tine;
   a septum extending between the opposing sides in the transition portion, the septum defining first and second floss paths within the housing, the first floss path extending between the septum and top and communicating with the first tine, the second floss path extending between the septum and bottom and communicating with the second tine, the septum positioned so that the first and second floss paths generally diverge from the head portion toward the handle portion;

a dental floss supply disposed within the handle portion; and a spool rotatably mounted within the handle and configured to securely hold a free end of the dental floss supply, the winding gear having at least a portion accessible from outside of the housing;

wherein floss from the winding gear extends into one of the first and second floss paths, through the first and second apertures and into the other of the first and second floss paths, and to the floss supply.

13. The hand-held flossing device of claim 12 additionally comprising a floss supply guide that directs floss from the floss supply toward the housing top, wherein a floss supply path is defined from the floss supply guide to the first floss path and to the first aperture, and a floss recovery path is defined from the second aperture to the second floss path and to the winding gear.

14. The hand-held flossing device of claim 13 additionally comprising a lock disposed in the housing along the floss supply path and moveable between a locked position and an unlocked position to selectively inhibit the advancement of floss beyond the lock.

15. The hand-held flossing device of claim 14, wherein the housing is configured so that floss changes direction about 180° along a path from the lock to the second aperture.

16. The hand-held flossing device of claim 15, wherein the housing is configured so that floss changes direction at least about 90° along a path from the second aperture to the winding gear.

17. The hand-held flossing device of claim 15, wherein the housing is configured so that floss changes direction more than about 90° along a floss path from the second aperture to the winding gear.

18. The hand-held flossing device of claim 17, wherein the floss path is completely enclosed within the housing except for the portion extending between the first and second apertures.

* * * * *